United States Patent [19]
Ichikawa et al.

[11] 3,957,887
[45] May 18, 1976

[54] PROCESS FOR PREPARING TRIMETHYLHYDROQUINONE

[75] Inventors: Yataro Ichikawa; Yoshiyuki Yamanaka; Hideki Tsuruta, all of Iwakuni, Japan

[73] Assignee: Teijin Ltd., Osaka, Japan

[22] Filed: Aug. 27, 1973

[21] Appl. No.: 391,667

[30] Foreign Application Priority Data
Sept. 18, 1972 Japan................................ 47-92842

[52] U.S. Cl............................ 260/621 R; 260/586 R
[51] Int. Cl.$^2$........................................ C07C 37/00
[58] Field of Search..................... 260/621 R, 621 H

[56] References Cited
UNITED STATES PATENTS
3,487,117  12/1969  Altwicker........................ 260/621 R Primary Examiner—Norman Morgenstern
Attorney, Agent, or Firm—Sherman & Shalloway

[57] ABSTRACT

This invention is directed to a process for preparing trimethylhydroquinone (TMHQ) by heating 4-hydroxy-2,4,6-trimethyl-2,5-cyclohexadiene-1-one (HTCD) in a nonacidic liquid medium consisting of either methanol or an aqueous medium, preferably in the presence of a basic substance, at a temperature of at least 100°C., and preferably 150°–300°C.

Thus, according to this invention, TMHQ of high purity and small coloration can be prepared from HTCD in good yield, for example, as high as 85 – 98%.

8 Claims, No Drawings

PROCESS FOR PREPARING TRIMETHYLHYDROQUINONE

This invention relates to a process for preparing trimethylhydroquinone. More particularly, the invention relates to a process for preparing trimethylhydroquinone by the intramolecular rearrangement of 4-hydroxy-2,4,6-trimethyl-2,5-cyclohexadiene-1-one.

The process of the invention can be shown by the following reaction equation (1):

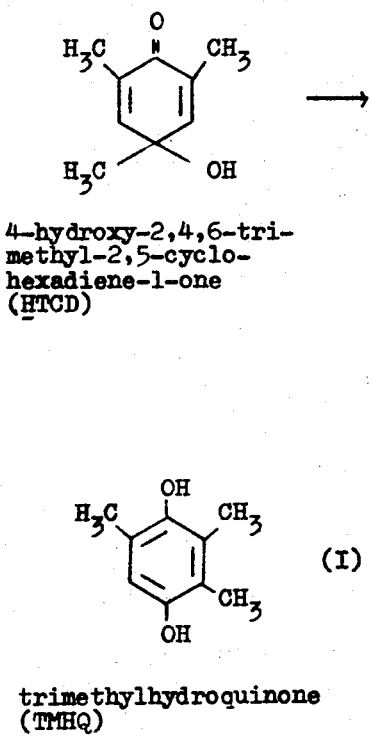

Processes for preparing trimethylhydroquinone by the intramolecular rearrangement of 4-hydroxy-2,4,6-trimethyl-2,5-cyclohexadiene-1-one have been proposed in the past in such publications as, for example, The Journal of Organic Chemistry, Japan, Vol. 25, 252 (1967), Ber 33 3600 (1900) and Med. Prom. S. S. S. R. 14 27 (1960).

However, in all of these hitherto-proposed processes the foregoing rearrangement reaction was carried out at a temperature of 90° – 95°C., and the reaction time was long. In addition, not only was the yield of trimethylhydroquinone low, but it also was obtained as a product having a brown to blackish brown coloration. Hence, these processes cannot be considered as being commercially advantageous processes.

It is therefore an object of the present invention to provide a process by which trimethylhydroquinone (TMHQ) can be obtained in good yield by the rearrangement of 4-hydroxy-2,4,6-trimethyl-2,5-cyclohexadiene-1-one (HTCD).

Another object of the invention is to provide a process for preparing in good yield from HTCD nondiscolored, white to light yellowish white TMHQ.

A further object of the invention is to provide a process which can produce TMHQ of high purity in good yield with a commercially inexpensive method.

Other objects and advantages of the invention will become apparent from the description which follows.

According to this invention, the foregoing objects and advantages are achieved essentially by heating 4-hydroxy-2,4,6-trimethyl-2,5-cyclohexdiene-1-one (HTCD) in a nonacidic liquid medium selected from the group consisting of methanol and an aqueous medium at a temperature of at least 100°C. and thereafter recovering the resulting trimethylhydroquinone (TMHQ).

The invention will be more fully described below.

The 4-hydroxy-2,4,6-trimethyl-2,5-cyclohexadiene-1-one (HTCD) to be used as the starting material in the present invention may be one that has been obtained by any method. As specific examples of the methods of obtaining HTCD, mention can be made of such as the following: (1) A method consisting of either reacting 2,4,6-trimethylphenol with a peracid such as Caro's acid or reacting 2,4,6-trimethylphenol with molecular oxygen in the presence of a basic reagent; (2) a method which consists in rearranging 1-hydroxyamino-2,4,6-trimethylbenzene; and (3) a method of oxidizing 2,4,6-trimethylphenol with molecular oxygen, the method that we previously proposed.

While the aforementioned HTCD to be used as the starting material of this invention may contain other substances which do not adversely affect the invention reaction, preferably used is HTCD of high purity for obtaining high purity TMHQ which is not discolored.

According to the present invention, this HTCD is heated in a nonacidic liquid medium selected from the group consisting of methanol and an aqueous medium at a temperature of at least 100°C. thereby accomplishing the rearrangement of HTCD shown by the aforesaid reaction equation (1).

By the expression "a nonacidic liquid medium", as used herein, is meant that the pH of said liquid medium is at least not less than 6.

In this invention, usable as the aqueous medium are either water or an aqueous solution of a water-soluble organic solvent. The water may be any that is usually available such as well water, river water, city water, ion-exchanged water, distilled water, etc. Well water and city water frequently have a pH of 6.1 – 6.8. In this invention water of such a pH is considered to be a nonacidic liquid medium. The invention can, of course, be practiced using water of such a pH.

On the other hand, as the aforementioned water-soluble organic solvent, any organic solvent will do so long as it is one which can form an aqueous solution whose pH at the least does not drop below 6 (i.e. is not acidic) on mixing with water, and which moreover is stable under the reaction conditions of the present invention. An aqueous solution of such an organic solvent in any proportion can be used as the liquid medium in this invention.

As such an organic solvent, included are such, for example, as a. The monohydric alcohols of 1 – 10 carbon atoms such, for example, as methanol, ethanol, n-propanol, iso-propanol, n-butanol, iso-butanol, t-butanol, amyl alcohol, octanol, methyl cellusolve and ethyl cellusolve;

b. The dihydric alcohols of 2 – 10 carbon atoms such, for example, as ethylene glycol, propylene glcyol and 1,4-butanediol; and the polyhydric alcohols such as glycerin;

c. The ketones such, for example, as acetone, methyl ethyl ketone and methyl isobutyl ketone;

d. The ethers such, for example, as tetrahydrofurane and dioxane;

e. The esters such, for example, as methyl acetate, ethyl acetate, propiolactone and methylbenzoate; and f. The amines such, for example, as trimethylamine, triethylamine, pyridine and pyrrolidone.

Of these organic solvents, especially suitable are the monohydric alcohols of 1 – 4 carbon atoms mentioned in (a), above, the ketones of 2 – 6 carbon atoms mentioned in (c), above, and the cyclic ethers such as mentioned in (d), above.

The aqueous solution of these organic solvents suitably contain water in an amount of at least 10% by weight, and preferably at least 20% by weight. And generally speaking, the aqueous solution becomes more suitable as the content of the water is increased.

However, methanol alone is an exception among these organic solvents. In the case of methanol, it can be used as the liquid medium in this invention regardless of whether it is substantially anhydrous or an aqueous solution in which water is contained in any proportion.

While the invention process, as previously indicated, consists in heating HTCD in a liquid medium, such as above described, at a temperature of at least 100°C. under nonacidic conditions, i.e., under conditions such that the pH at least does not fall below 6, in carrying out this process it is preferred that there is caused to be present in the reaction mixture a basic substance consisting of either an alkali metal or an alkaline earth metal, or a basic compound containing at least one of these metals in its molecular structure.

Usable as this basic substance are the alkali metals such, for example, as sodium, potassium, lithium, rubidium and cesium; the alkaline earth metals such, for example, as calcium, magnesium, barium, and strontium; as well as the basic compounds containing at least one of these metals in their molecular structure. As such basic compounds, mention can be made of such, for example, as the following compounds:

A. The hydroxides of alkali metals or alkaline earth metals such, for example, as sodium hydroxide, potassium hydroxide, lithium hydroxide, calcium hydroxide, magnesium hydroxide and barium hydroxide;

B. The carbonates and bicarbonates of alkali metals or alkaline earth metals such, for example, as sodium carbonate, sodium bicarbonate, potassium carbonate, potassium bicarbonate, calcium carbonate, barium carbonate and magnesium carbonate;

C. The oxides of alkaline earth metals such, for example, as calcium oxide, magnesium oxide and barium oxide; and D. The alkali metal- or alkaline earth metal-containing compounds that have hitherto been used as buffers such, for example, as a suitable mixture of an alkali dihydrogen phosphate such as monopotassium dihydrogen phosphate and a dialkali monohydrogen phosphate such as dipotassium monohydrogen phosphate, or the alkali metal salts of such organic carboxylic acids as boric acid, citric acid, lactic acid, tartaric acid and acetic acid.

The process of this invention is conveniently carried out under the conditions of pH at least not less than 6.5, and preferably at least not less than 7, and furthermore in the presence of a basic substance, such as hereinbefore described. A most preferred pH of the reaction mixture is 7 – 14.

Further, in practicing the invention process in the presence of the aforementioned basic substance, the lower limit of the amount to be added of the foregoing substance is determined by the amount sufficient to maintain the reaction system (reaction mixture) of the invention at a pH of at least 6, preferably at least 6.5, and especially advantageously at least 7, as hereinbefore indicated. However, when the amount added of the basic substance becomes too great, the coloration of the resulting TMHQ is increased, and the yield declines rather than being improved. Hence, it is an advantage to establish an upper limit to the amount that the aforesaid basic substance is added to ensure that its concentration in the reaction mixture does not exceed 1 normality, and preferably 0.1 normality.

As the basic substance, preferred are those which are soluble in the liquid medium that is used. And especially in the case where methanol is used as the medium, the hydroxides of alkali metals are advantageously used as the basic substance.

Further, the concentration of HTCD, the starting material in this invention, in the aforementioned liquid medium is also intimately related in preparing the intended THMQ in good yield. A concentration in the liquid medium of said HTCD of 0.1 – 20% by weight, preferably 0.5 – 10% by weight, and especially 1 – 7% by weight, is desirable.

Especially, when the reaction is carried out in such a manner that the concentration in the reaction mixture of the aforesaid basic substance does not exceed 0.1 normality and the concentration of the HTCD in the liquid medium is held at 0.5 – 10% by weight, and preferably 1 – 7% by weight, TMHQ of small coloration can be prepared in good yield.

Another important requisite for carrying out the present invention advantageously is the temperature conditions.

As previously indicated, in the instant invention, the heating of HTCD, the starting material, in the aforementioned nonacidic liquid medium at a temperature of at least 100°C. will do. While the upper limit of the heating temperature must be established in consideration of such relationships as the heating time of the starting HTCD and the residence time of the resulting TMHQ in the reaction system, in short, a temperature which does not cause excessive side reaction or result in excessive decomposition and discoloration of the resulting TMHQ may be used.

However, for obtaining in good yeild high purity TMHQ without its discoloration, the heating of the starting HTCD in the reaction system of the invention is advantageously carried out in the range of 120° – 350°C., and especially 150° – 300°C., the optimum range of the heating temperature being 180° – 270°C.

When the process of the invention is carried out in an aqueous medium under the foregoing preferred temperature conditions, for example, a temperature in the range of 150° – 300°C., preferably 180° – 270°C., and moreover using as the aforesaid basic substance a suitable alkali metal or a hydroxide thereof at a concentration in the reaction mixture ranging 0.0001 – 0.1 normality, particularly 0.0001 – 0.1 normality (as pH, a range of approximately 10 – 13, especially 11 – 13), the intended TMHQ can be obtained in good yield. In addition, since the coloration of the resulting TMHQ is exceedingly small, the process is of great advantage.

Furthermore, the above reaction is preferably carried out in the presence of a reducing substance, because it can give TMHQ of further reduced coloration. Examples of the reducing substance are sodium sulfate ($Na_2SO_3$), sodium bisulfite ($NaHSO_3$), hydrosulfite ($Na_2S_2O_4$), and sodium thiosulfate ($Na_2S_2O_3$), the first-mentioned being especially preferred.

In practicing the invention process, the reaction is carried out with the reaction system being charged with a liquid atmosphere maintained at a plenum, or the reaction system is held under a vaporous atmosphere of the liquid medium or an atmosphere of a gas inert to the reaction, e.g., nitrogen, helium, argon, methane, etc. In general, the presence of oxygen not only greatly interferes with the reaction and causes a decline in the yield but also becomes the cause of discoloration of the product. Hence, the invention process should be carried out in a nonacidic atmosphere. While the reaction may be carried out at normal atmospheric or superatmospheric pressures so long as the pressure used is one which can maintain the reaction system in the liquid phase, usually used is a pressure of less than 300 kg/cm²G, preferably less than 100 kg/cm²G, and more preferably less than 50 kg/cm²G.

The process of this invention may be carried out by either the batchwise or continuous method.

According to the invention, the trimethylhydroquinone (TMHQ) is thus obtained in its free form and/or the form of an alkali metal salt or an alkaline earth metal salt. The extent to which the trimethylhydroquinone becomes such a salt of an alkali metal or alkaline earth metal depends upon the amount of the aforesaid basic substance that is used in carrying out the invention process.

However, trimethylhydroquinone has a tendency to discolor and turn to a brown or black color when exposed to air in its moist state and moreover in the presence of an alkaline substance.

Hence, in order to isolate and recover the trimethylhydroquinone from the reaction product obtained by the invention process, a preferred procedure is that comprising adding an acid such, for example, as hydrochloric, sulfuric or acetic acid to the reaction product to at least neutralize the basic substance contained in the reaction product while, on the other hand, the alkali metal and/or alkaline earth metal salts of said TMHQ is converted to free TMHQ, and thereafter the TMHQ is isolated and recovered from the reaction mixture.

In the case where the liquid medium used in carrying out the reaction is an aqueous medium, since TMHQ is insoluble in such an aqueous medium, it can be isolated and recovered from the reaction mixture by the known solid-liquid separation procedures such as, say, filtration, centrifugation, etc.

On the other hand, when methanol or an aqueous organic solvent solution whose concentration of the organic solvent is great is used as the liquid medium, the reaction mixture obtained by the invention process can be isolated and recovered in the following manner. The reaction mixture is treated with an acid as hereinbefore described, and then it is submitted to such a procedure as, say, distillation, etc., to recover the liquid medium as well as concentrate the reaction mixture, after which the concentrated reaction mixture is added with water, if necessary, and the TMHQ separated out is isolated and recovered by the known solid-liquid separation techniques.

The isolation and recovery of TMHQ from the reaction product obtained in accordance with the present invention is not limit to the hereinbefore-described methods, however, but may carried out by any of the known methods.

Thus, it is possible by operating as hereinbefore described to prepare in good yield high purity trimethylhydroquinone of small coloration in accordance with the present invention. Trimethylhydroquinone is an important intermediate for the synthesis of, say, vitamins, and it itself can be used as an antioxidant or polymerization inhibitor.

The following examples are given for more fully illustrating the process of this invention, but the invention is not to be limited thereby. Unless otherwise specified, the parts in the examples are on a weight basis. The optical density (O.D.), as used in the examples, was determined in the following manner.

1. When the reaction has been carried out in a sealed tube.

After completion of the reaction, the tube is opened and the reaction product is precipitated with acid. The total contents are placed in a 50-cc volumetric flask followed by adding methanol to dissolve the reaction product and dilute the solution to make the total quantity 50 cc. This is used as the specimen, and its absorbance at a wavelength of 400 m$\mu$ is determined with a 1-cm cell, using methanol as the reference liquid.

2. When the reaction has been carried out in an autoclave.

After completion of the reaction, the separated cake is dried. Using this as the specimen, 100 mg thereof is weighed and placed in a 25-cc volumetric flask. Acetic acid is then added to dissolve the specimen and dilute the solution to make the total quantity 25 cc. This is used as the specimen, and its absorbance at a wavelength of 400 m$\mu$ is determined with a 1-cm cell, using acetic acid as the reference liquid.

EXAMPLE 1

0.06 Part of 4-hydroxy-2,4,6-trimethyl-2,5-cyclohexadiene-1-one (HTCD) was placed in a sealable tube and, after adding 3 parts of a 3% aqueous NaOH solution and thorough purging of the tube with nitrogen, the tube was sealed. The tube was then shaken for 10 minutes in a 160°C. oil bath, after which the tube was immediately opened in a nitrogen atmosphere, and the reaction product was acidified with 2N $H_2SO_4$.

On analysis of the reaction product, it was found that 0.057 part of trimethylhydroquinone had been obtained at a yield of 95%.

EXAMPLE 2

0.06 Part of 4-hydroxy-2,4,6-trimethyl-2,5-cyclohexadiene-1-one (HTCD) was placed in a sealable tube, after which 3 parts of a nitrogen-purged aqueous caustic soda solution of a concentration indicated in the following Table 1 was added. The tube was then thoroughly purged with nitrogen and sealed. The concentration of HTCD in the starting mixture was about 2 weight % based on the water in this case, while the concentration of caustic soda was about 0.75 N. The tube was then shaken in an oil bath at a temperature and for a period of time such as indicated in the following Table 1. After completion of the reaction, the reaction product was treated and analyzed as in Example 1 with the results shown in Table 1, below.

tion of a metal compound varying in class as indicated in the following Table 3 was added. The tube was then Table 1

| Run No. | Reaction temperature (°C.) | Reaction time (min) | pH | NaOH/ start. mat. (mol) | NaOH concentration (N) | Start. mat./ medium (weight %) | Intended product (part) | Yield product (%) | O.D. 400 mμ | Remarks |
|---|---|---|---|---|---|---|---|---|---|---|
| 2-a | 90 | 120 | >13 | 5.7 | 0.75 | 2 | 0.047 | 78.3 | 0.609 | Control |
| 2-b | 90 | 120 | ~12 | 0.076 | 0.01 | '' | 0.026 | 43.5 | 0.130 | '' |
| 2-c | 100 | 20 | >13 | 5.7 | 0.75 | '' | 0.050 | 82.7 | 0.068 | invention |
| 2-d | 100 | 30 | '' | '' | '' | '' | 0.051 | 85.2 | 0.070 | '' |
| 2-e | 100 | 40 | '' | '' | '' | '' | 0.052 | 86.8 | 0.076 | '' |
| 2-f | 100 | 80 | '' | '' | '' | '' | 0.053 | 88.3 | 0.080 | '' |
| 2-g | 110 | 10 | '' | '' | '' | '' | 0.049 | 82.8 | 0.085 | '' |
| 2-h | 120 | 10 | '' | '' | '' | '' | 0.049 | 82.8 | 0.090 | '' |
| 2-i | 130 | 10 | '' | '' | '' | '' | 0.051 | 85.0 | 0.095 | '' |
| 2-j | 130 | 60 | '' | '' | '' | '' | 0.053 | 88.5 | 0.101 | '' |
| 2-k | 140 | 10 | '' | '' | '' | '' | 0.053 | 88.2 | 0.101 | '' |
| 2-l | 150 | 10 | '' | '' | '' | '' | 0.055 | 92.2 | 0.115 | '' |
| 2-m | 150 | 60 | '' | '' | '' | '' | 0.055 | 92.2 | 0.325 | '' |
| 2-n | 170 | 10 | '' | '' | '' | '' | 0.054 | 89.3 | 0.140 | '' |
| 2-o | 200 | 10 | ~12 | 0.076 | 0.01 | '' | 0.058 | 95.7 | 0.031 | '' |
| 2-p | 250 | 10 | '' | '' | '' | '' | 0.059 | 97.9 | 0.037 | '' |
| 2-q | 300 | 10 | '' | '' | '' | '' | 0.051 | 84.7 | 0.048 | '' |

EXAMPLE 3

0.06 Part of HTCD was placed in a sealable tube, after which 3 parts of a nitrogen-purged aqueous solution of a metal compound varying in class as indicated in the following Table 2 was added. The tube was then thoroughly purged with nitrogen and sealed. The sealed tube was then shaken in an oil bath for a period of time and at a temperature such as indicated in Table 2. After completion of the reaction, the reaction mixture was treated as in Example 1 and analyzed with the results shown in Table 2, below.

Table 2

| Run No. | Reaction temperature (°C.) | Reaction time (min.) | pH | Metal compd./ Start. mat. (mol) | Metal compd. concentration (N) | Start. mat./ medium (weight %) | Intended product (part) | Yield product (%) | O.D. 400 mμ | Class of metal compd. |
|---|---|---|---|---|---|---|---|---|---|---|
| 3-a | 250 | 10 | ~12 | 0.076 | 0.01 | 2 | 0.054 | 89.5 | 0.160 | KOH |
| 3-b | 250 | 10 | >12 | 0.17 | 0.02 | '' | 0.057 | 94.7 | 0.091 | Ca(OH)$_2$ |
| 3-c | 250 | 10 | ~12 | 0.04 | 0.01 | '' | 0.058 | 93.8 | 0.085 | Ba(CH$_2$) |
| 3-d | 250 | 10 | >12 | 0.25 | 0.03 | '' | 0.050 | 83.0 | 0.068 | CH$_3$COONa |

EXAMPLE 4

0.12 Part of HTCD was placed in a sealable tube, after which 3 parts of a nitrogen-purged aqueous solution of a metal compound varying in class as indicated in the following Table 3 was added. The tube was then thoroughly purged with nitrogen and sealed. The sealed tube was then shaken in an oil bath at a temperature and for a period of time such as indicated in Table 3. After completion of the reaction, the reaction mixture was treated as in Example 1 and analyzed with the results shown in Table 3, below.

Table 3

| Run No. | Reaction temperature (°C.) | Reaction time (min.) | pH | Class of metal Compd. | Metal compd./ Start. mat. (mol) | Metal compd. concentration (N) | Start. mat./ medium (weight %) | Intended product (g) | Yield product (%) | O.D. 400 mμ |
|---|---|---|---|---|---|---|---|---|---|---|
| 4-a | 250 | 10 | 9.9 | Na$_2$CO$_3$ | 0.038 | 0.02 | 4 | 0.111 | 92.3 | 0.075 |
| 4-b | 250 | 10 | 7.7 | NaHCO$_3$ | 0.038 | 0.01 | 4 | 0.117 | 97.5 | 0.050 |

EXAMPLE 5

0.09 Part of HTCD, caustic soda in a proportion indicated in the following Table 4, and water were used, and by operating as in Example 1 the reaction was carried out at a temperature and for a period of time such as indicated in said table. After completion of the reaction, the reaction mixture was analyzed with the results shown in Table 4, below.

Table 4

| Run No. | Reaction temperature (°C.) | Reaction time (min) | pH | NaOH/ Start. mat. (mol) | NaOH concentration (N) | Start. mat./ medium (weight %) | Intended product (part) | Yield product (%) | O.D. 400 mμ |
|---|---|---|---|---|---|---|---|---|---|
| 5-a | 160 | 10 | >13 | 2.5 | 0.5 | 3 | 0.078 | 86.4 | 0.195 |
| 5-b | 160 | 10 | '' | 3.8 | 0.75 | '' | 0.080 | 89.0 | 0.240 |
| 5-c | 160 | 20 | '' | 3.8 | 0.75 | '' | 0.077 | 85.9 | 0.210 |
| 5-d | 160 | 10 | >14 | 6.3 | 1.25 | '' | 0.079 | 87.5 | 0.200 |
| 5-e | 160 | 10 | '' | 12.7 | 2.5 | '' | 0.075 | 83.5 | 0.130 |
| 5-f | 200 | 10 | ~12 | 0.076 | 0.01 | '' | 0.084 | 93.7 | 0.035 |

Table 4-continued

| Run No. | Reaction temperature (°C.) | Reaction time (min) | pH | NaOH/ Start. mat. (mol) | NaOH concentration (N) | Start. mat./ medium (weight %) | Intended product (part) | Yield product (%) | O.D. 400 mµ |
|---|---|---|---|---|---|---|---|---|---|
| 5-g | 250 | 10 | ~13 | 0.76 | 0.1 | " | 0.079 | 87.7 | 0.040 |
| 5-h | 250 | 10 | ~12 | 0.076 | 0.01 | " | 0.087 | 96.7 | 0.034 |

EXAMPLE 6

The reaction was carried out under the conditions indicated in the following Table 5, using 0.12 part of HTCD, caustic soda in a proportion indicated in said table, and water. After completion of the reaction, the reaction mixture was analyzed with the results shown in Table 5, below.

Table 5

| Run No. | Reaction temperature (°C.) | Reaction time (min.) | pH | NaOH/ Start. mat. (mol) | NaOH concentration (N) | Start. mat./ medium (weight %) | Intended product (part) | Yield product (%) | O.D. 400 mµ |
|---|---|---|---|---|---|---|---|---|---|
| 6-a | 160 | 10 | >13 | 2.9 | 0.75 | 4 | 0.107 | 89.3 | 0.223 |
| 6-b | 160 | 10 | >14 | 4.8 | 1.25 | " | 0.097 | 81.1 | 0.325 |
| 6-c | 160 | 10 | " | 9.5 | 2.50 | " | 0.102 | 85.4 | 0.215 |
| 6-d | 160 | 10 | " | 14.3 | 3.75 | " | 0.104 | 86.7 | 0.145 |
| 6-e | 200 | 10 | ~12 | 0.076 | 0.01 | " | 0.110 | 91.5 | 0.033 |
| 6-f | 230 | 10 | " | 0.076 | 0.01 | " | 0.117 | 97.5 | 0.033 |
| 6-g | 250 | 10 | " | 0.076 | 0.01 | " | 0.107 | 89.2 | 0.060 |

EXAMPLE 7

The reaction was carried out under the conditions indicated in the following Table 6, using 0.15 part of HTCD, caustic soda in a proportion indicated in said table, and water. After completion of the reaction, the reaction mixture was analyzed with the results shown in Table 6, below.

Table 6

| Run No. | Reaction temperature (°C.) | Reaction time (min.) | pH | NaOH/ Start. mat. (mol) | NaOH Concentration (N) | Start. mat./ medium (weight %) | Intended product (part) | Yield product (%) | O.D. 400 mµ |
|---|---|---|---|---|---|---|---|---|---|
| 7-a | 160 | 20 | >14 | 3.8 | 1.25 | 5 | 0.118 | 78.9 | 0.760 |
| 7-b | 160 | 30 | " | 3.8 | 1.25 | " | 0.120 | 80.0 | 1.200 |
| 7-c | 160 | 40 | " | 3.8 | 1.25 | " | 0.119 | 79.0 | 0.720 |
| 7-d | 160 | 10 | " | 7.6 | 2.50 | " | 0.126 | 84.2 | 0.470 |
| 7-e | 160 | 20 | " | 7.6 | 2.50 | " | 0.125 | 83.3 | 0.440 |
| 7-f | 160 | 30 | " | 7.6 | 2.50 | " | 0.120 | 79.7 | 0.850 |
| 7-g | 160 | 40 | " | 7.6 | 2.50 | " | 0.120 | 79.7 | 0.850 |
| 7-h | 200 | 10 | ~12 | 0.076 | 0.01 | " | 0.136 | 90.7 | 0.065 |
| 7-i | 250 | 10 | " | 0.076 | 0.01 | " | 0.125 | 86.0 | 0.082 |

EXAMPLE 8

The reaction was carried out under the conditions indicated in the following Table 7, using 0.18 part of HTCD, caustic soda in a proportion indicated in said table, and water. After completion of the reaction, the reaction mixture was analyzed with the results shown in Table 7, below.

Table 7

| Run No. | Reaction temperature (°C.) | Reaction time (min) | pH | NaOH/ Start. mat. (mol) | NaOH Concentration (N) | Start. mat./ medium (weight %) | Intended product (part) | Yield product (%) | O.D. 400 mµ |
|---|---|---|---|---|---|---|---|---|---|
| 8-a | 160 | 30 | >13 | 1.9 | 0.75 | 6 | 0.140 | 78.0 | 0.840 |
| 8-b | 160 | 10 | >14 | 3.2 | 1.25 | " | 0.141 | 78.4 | 0.740 |
| 8-c | 160 | 10 | >14 | 6.3 | 2.50 | " | 0.159 | 88.1 | 0.990 |
| 8-d | 160 | 10 | >14 | 9.5 | 3.75 | " | 0.149 | 83.0 | 0.550 |

EXAMPLE 9

The reaction was carried out in methanol under the conditions indicated in the following Table 8, using 0.06 part of HTCD and a catalyst shown in said table. After completion of the reaction, the reaction mixture was analyzed with the results shown in Table 8, below.

Table 8

| Run No. | Reaction temperature (°C.) | Reaction time (min.) | Catalyst | Cat./ Start. mat. (mol) | NaOH Concentration (mol/l) | Start. mat./ medium (weight %) | Intended product (part) | Yield product (%) | O.D. 400 mµ |
|---|---|---|---|---|---|---|---|---|---|
| 9-a | 250 | 10 | NaOH | 0.076 | 0.001 | 2 | 0.055 | 92.3 | 0.060 |

Table 8-continued

| Run No. | Reaction temperature (°C.) | Reaction time (min.) | Catalyst | Cat./Start. mat. (mol) | NaOH Concentration (mol/l) | Start. mat./medium (weight %) | Intended product (part) | Yield product (%) | O.D. 400 mμ |
|---|---|---|---|---|---|---|---|---|---|
| 9-b | " | " | KOH | 0.076 | " | " | 0.052 | 86.7 | 0.337 |
| 9-c | " | " | CH₃COONa | 0.25 | " | " | 0.054 | 90.8 | 0.326 |
| 9-d | " | " | CH₃COOK | 0.25 | " | " | 0.051 | 85.3 | 0.545 |
| 9-e | " | " | NaHCO₃ | 0.15 | " | " | 0.053 | 88.3 | 0.524 |
| 9-f | " | " | Na₂CO₃ | 0.12 | " | " | 0.056 | 92.7 | 0.310 |
| 9-g | " | " | KHCO₃ | 0.12 | " | " | 0.054 | 90.5 | 0.250 |

EXAMPLE 10

0.06 Part of HTCD and 0.0012 part of caustic soda were placed in a sealable tube, to which was then added 3 parts of a nitrogen-purged solvent mixture shown in the following Table 9. The tube was then thoroughly purged and sealed. This was followed by shaking the sealed tube for 10 minutes in an oil bath of 250°C. After completion of the reaction, the reaction mixture was withdrawn from the tube and analyzed with the results shown in Table 9, below.

Table 9

| Run No. | Cat./Start. mat. (mol %) | Start. mat./medium (weight %) | Solvent mixture (1:1 wt. ratio) | Intended product (part) | Yield product (%) | O.D. (400 mμ) |
|---|---|---|---|---|---|---|
| 10-a | 0.076 | 2 | acetone:water | 0.049 | 81.5 | 0.100 |
| 10-b | " | " | pyridine:water | 0.053 | 88.3 | 0.210 |
| 10-c | " | " | methanol:water | 0.055 | 92.3 | 0.060 |
| 10-d | " | " | T.H.F:water | 0.053 | 87.8 | 0.246 |
| 10-e | " | " | dioxane:water | 0.052 | 92.0 | 0.145 |
| 10-f | " | " | 1,4-butanediol:water | 0.056 | 93.3 | 0.188 |
| 10-g | " | " | t-BuOH:water | 0.057 | 95.0 | 0.275 |

EXAMPLE 11

A steel autoclave equipped with a stirrer, a gas inlet line and a temperature recording device was charged with 8.0 parts of HTCD and 200 parts of a caustic soda solution of pH 12.3, after which the autoclave was thoroughly purged with nitrogen, and the temperature was raised. When the internal temperature reached 250°C., it was held there for 10 minutes. After completion of the reaction, the reaction mixture was cooled and, while passing in nitrogen, precipitated by means of dilute sulfuric acid. When the resulting cake was filtered and dried, 6.1 parts of the cake was obtained. Since 1.0 part of TMHQ was contained in the filtrate in this case, the yield of this reaction was 88.8%.

The so obtained TMHQ has an optical density of 0.39 at a wavelength of 400 mμ and a melting point of 171.5°C. The findings of the infrared analysis (I. R.) and nuclear magnetic resonance spectrum (N. M. R.) are shown in Table 10, below.

Table 10

| I.R. $\nu_{max.}^{KBr}$ | N. M. R. δ(ppm) |
|---|---|
| 3305 cm⁻¹ >—OH | 7.3 (m. vinylproton in 3-position) |
| 1210 cm⁻¹ | 6.4 (m. —OH) |
| 850 cm⁻¹ | 2.1 (s. methyl in 2,5,6-position |

EXAMPLE 12

A steel autoclave equipped with a stirrer, a gas inlet, and a temperature recording device was charged with 8 parts of HTCD, 192 parts of an aqueous solution of sodium hydroxide having a pH of 12.2, and 0.2 part of Na₂SO₃. The inside of the autoclave was purged sufficiently with nitrogen, and when the inside temperature reached 250°C., the reaction mixture was maintained at this temperature for 10 minutes. After the reaction, the reaction product was cooled, and precipitated with dilute sulfuric acid while passing nitrogen. The resulting cake was filtered and dried to form 7.4 parts of cake. Since the filtrate contained 1.0 part of TMHQ, the yield in this reaction was 92%. The results are shown in Table 8 below together with those of a control example.

Table 8

| Run No. | 12-a | 12-b |
|---|---|---|
| Reaction temperature (°C.) | 250 | 250 |
| Reaction time (min.) | 10 | 10 |
| Catalyst | NaOH | NaOH |
| Catalyst/material (mol ratio) | 0.057 | 0.057 |
| pH | 12.2 | 12.2 |
| Concentration of Na₂SO₃ (wt. %) | 0.1 | 0 |
| Material/medium (wt. %) | 4 | 4 |
| Product (parts) | 7.44 | 7.36 |
| Yield of product (%) | 93 | 92 |
| O. D. (400mμ) | 0.006 | 0.015 |

What is claimed is:

1. A process for preparing trimethylhydroquinone which comprises heating 4-hydroxy-2, 4, 6-trimethyl-2, 5-cyclohexadiene-1-one under an inert gas atmosphere and in a non-acidic liquid medium having a pH value of 7 to 14 selected from the group consisting of methanol and an aqueous medium selected from the group consisting of water and an aqueous solution of a water-soluble organic solvent at a temperature of 150°C to 300°C and in the presence of a basic substance which is non-reactive and soluble in said non-acidic liquid medium, said water-soluble organic solvent being selected from the group consisting of (A) monohydric alcohols of 1–10 carbon atoms, (B) dihydric alcohols of 2–10 carbon atoms, (C) alkanones of 3–6 carbon atoms, (D) ethers selected from the group consisting of tetrahydrofuran and dioxane, (E) esters selected from the group consisting of methyl acetate, ethyl acetate, propiolactone and methylbenzoate, and (F) amines selected from the group consisting of trimethylamine, triethylamine, pyridine and pyrrolidone, and said basic substance being selected from the group consisting of (a) hydroxides of alkali metals, (b) hydroxides of alkaline earth metals, (c) carbonates and bicarbonates of alkali metals, (d) carbonates and bicarbonates of alkaline earth metals, (e) oxides of alkaline earth metals, (f) alkali dihydrogen phosphate and dialkali hydrogen phosphate, and (g) alkali metal salts of boric acid, citric acid, lactic acid, tartaric acid or acetic acid.

2. The process of claim 1 which comprises controlling the concentration of said basic substance in the reaction mixture such that one normality is not exceeded.

3. The process of claim 1 wherein the concentration of said basic substance in the reaction mixture is controlled such that 0.1 normality is not exceeded.

4. The process of claim 1 which comprises using said 4-hydroxy-2,4,6-trimethyl-2,5-cyclohexadiene-1-one in the reaction mixture in a concentration of 0.1 – 20 percent by weight based on said liquid medium.

5. The process of claim 1 which comprises using said 4-hydroxy-2,4,6-trimethyl-2,5-cyclohexadiene-1-one in the reaction mixture in a concentration of 0.5 – 10 percent by weight based on said liquid medium.

6. The process of claim 1 wherein said non-acidic liquid medium is said aqueous solution of water-soluble organic solvent containing water in an amount of at least 10 percent by weight.

7. The process of claim 1 which comprises heating said 4-hydroxy-2,4,6-trimethyl-2,5-cyclohexadiene-1-one at a temperature ranging between 180°C and 270°C.

8. The process of claim 1 wherein said non-acidic liquid medium is methanol.

* * * * *